United States Patent [19]

Cragoe, Jr. et al.

[11] 3,984,552

[45] Oct. 5, 1976

[54] 6-OXO-7-SUBSTITUTED AND 7,7-DISUBSTITUTED-6H-INDENO-[5,4-B]FURAN (AND THIOPHENE) CARBOXYLIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: Feb. 24, 1975

[21] Appl. No.: 552,402

[52] U.S. Cl. .................. 424/250; 260/247.1 P; 260/293.57; 260/293.58; 260/330.5; 260/346.2 M; 424/248; 424/267; 424/275; 424/285; 260/247.7 R; 260/247.7 T; 260/247.7 V
[51] Int. Cl.$^2$ ..................................... C07D 307/83
[58] Field of Search ............. 260/330.5, 346.2 M, 260/247.1 P, 247.7 F, 293.57, 293.58; 424/268, 248, 275, 285, 250

[56] References Cited
UNITED STATES PATENTS
3,931,239   1/1976   Cragoe et al. ............... 260/346.2 M

*Primary Examiner*—Natalie Trousof
*Assistant Examiner*—C. M. S. Jaisle
*Attorney, Agent, or Firm*—Michael C. Sudol, Jr.

[57] ABSTRACT

6-Oxo-7,7-disubstituted-1,2,7,8-tetrahydro (and 7,8-dihydro)-6H-indeno-[5,4-b]furan (and thiophene)carboxylic acids, the salt, ester and amide derivatives thereof and combinations of these compounds with antikaluretic agents are disclosed having diuretic-saluretic, uricosuric and antihypertensive activity.

15 Claims, No Drawings

6-OXO-7-SUBSTITUTED AND 7,7-DISUBSTITUTED-6H-INDENO-[5,4-B]FURAN (AND THIOPHENE) CARBOXYLIC ACIDS

BACKGROUND OF THE INVENTION

This invention relates to certain indenofurans and indenothiophenes having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation of symptoms associated with electrolyte imbalance and fluid retention such as edema associated with hypertension.

The compounds of this invention may be represented by the following generic structure:

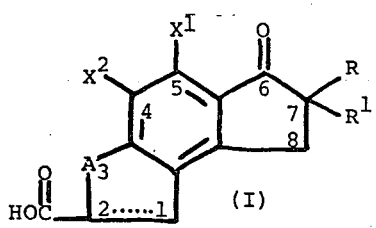

wherein the dotted line indicates 1,2-saturated or unsaturated embodiments; A is oxygen or sulfur; R is aryl, substituted aryl, thienyl or substituted thienyl; $R^1$ is lower alkyl, $X^1$ is lower alkyl or halo; $X^2$ is hydrogen, lower alkyl or halo.

Also within the scope of the present invention are the respective salt, ester and amide derivatives of the above-described compounds.

For convenience, these compounds will collectively be referred to hereinafter as "indenofurans".

The pharmacological studies show that the instant products are effective diuretic, saluretic and uricosuric agents which can be used in the treatment of conditions associated with electrolyte and fluid retention in the treatment of hypertension. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

Thus it is an object of the present invention to provide the indenofurans of the above general description and to provide processes for preparation of such compounds. Further objects of this invention are to provide pharmaceutical compositions comprising such indenofurans and to provide methods of treatment comprising administering such compounds and compositions.

DETAILED DESCRIPTION OF THE INVENTION

For purposes of description, the indenofurans of the present invention (Structure I above) may be represented according to the following structural formulae:

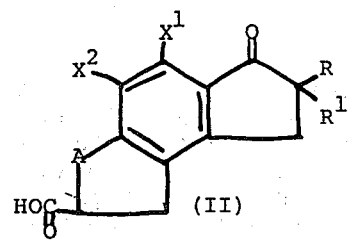

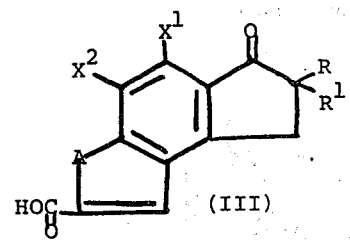

wherein A, $X^2$, $X^1$, R and $R^1$ have previously been defined.

The preferred indenofurans of the present invention are those wherein A is oxygen; R is aryl such as phenyl and substituted aryl wherein the substituent is lower alkyl or halo; thienyl and substituted thienyl wherein the substituent is lower alkyl or halo; $R^1$ is lower alkyl having from 1 to about 6 carbon atoms; $X^1$ is lower alkyl having from 1 to about 6 carbon atoms, or halogen such as chloro, fluoro and bromo; $X^2$ is hydrogen, lower alkyl having from 1 to about 6 carbon atoms, or halogen such as chloro, fluoro and bromo.

The more preferred indenofurans of the present invention are those wherein A is oxygen; R is phenyl, p-chlorophenyl or thienyl; $R^1$ is lower alkyl having from 1 to 3 carbon atoms; $X^1$ is chloro or methyl and $X^2$ is hydrogen, chloro or methyl.

Of the non-toxic pharmaceutically acceptable salt, ester and amide derivatives of (I), the preferred salts are those of ammonia, amines and of the alkali metals—principally sodium and potassium; the preferred esters are those derived from lower alkanols having from 1 to about 6 carbon atoms; the preferred amides are those derived from mono-and di-lower alkyl amines and hetero amines such as piperidine, morpholine and the like.

The indenofurans of the present invention may be prepared essentially by two basic schemes of synthesis, B and C.

Central to scheme B is an appropriate substituted 5-methoxyindanone derivative having the structure:

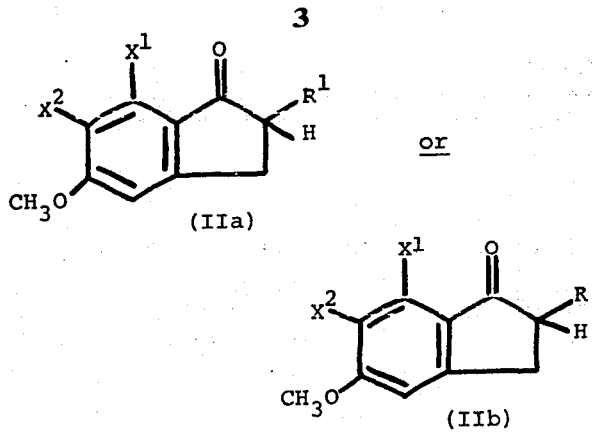

wherein $X^1$, $X^2$, R and $R^1$ have been previously defined. The preparation of representative indanones of structure (IIa) have been fully disclosed in Belgian Pat. No. 806,036 (Apr. 12, 1974). Indanones of structure (IIb) are prepared by Friedel-Crafts reaction of appropriately substituted anisole, followed by a modified Mannich reaction and cyclialkylation as set forth in Scheme A. Scheme A may generally be depicted in the following manner:

According to Scheme A, an appropriately substituted anisole (Ia) is reacted under Friedel-Crafts conditions with a carboxylic acid halide (Ib) wherein R has been previously defined and Z is halogen such as chloro or bromo to yield the 4-acyl specie (Ic). Suitable catalysts for the reaction are aluminum chloride, tin chloride and the like. The reaction solvent and temperature are not critical inasmuch as any solvent which is inert to the acyl halide/anisole reactants may be employed. In this regard, suitable solvents include aliphatic and cycloaliphatic hydrocarbons such as heptane, cyclohexane, and the like; carbon disulfide and halogenated hydrocarbons such as carbon tetrachloride, methylene chloride, and the like. Typically the reaction is conducted at from 0°C. to the reflux temperature of the particular solvent employed, the preferred condition being carbon disulfide at 0°C.

The Friedel-Crafts product (Ic) is converted to the 2'-methylene derivative (Id) via a modified Mannich reaction by treating (Ic) with bis(dimethylamino)methane in the presence of acetic anhydride. Cyclialkylation of (Id) in the presence of a Lewis acid such as sulfuric acid, trifluoroacetic acid or polyphosphoric acid gives (IIb).

Scheme B may be generally depicted in the following manner:

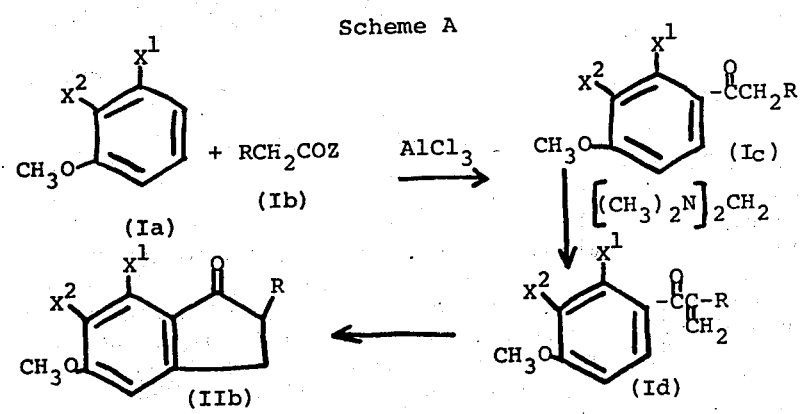

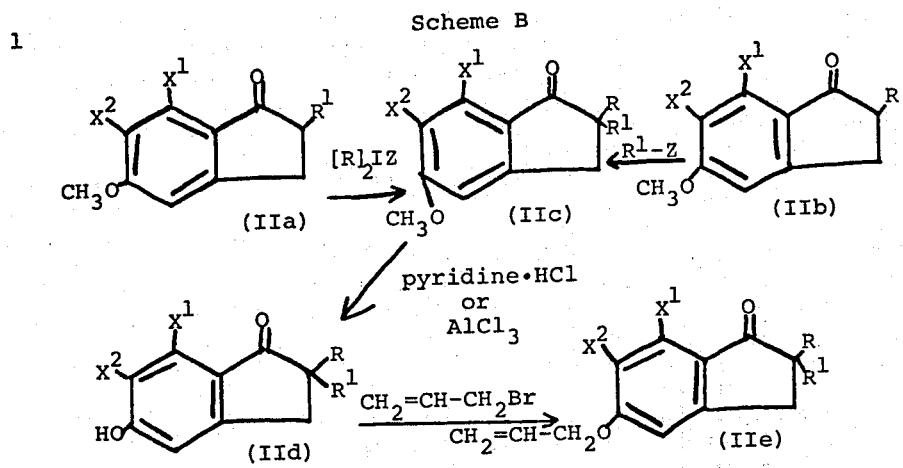

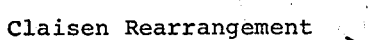
Claisen Rearrangement

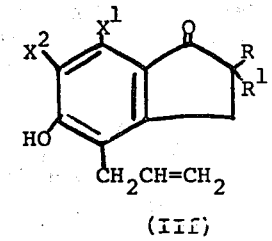

(IIf)

peracid

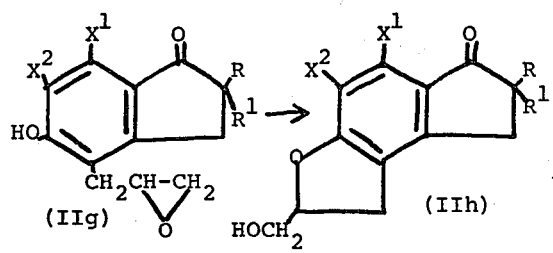

oxidation

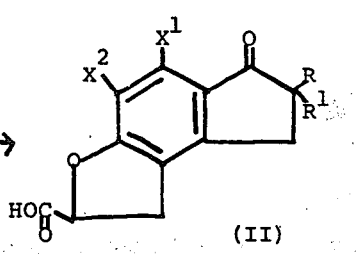

According to Scheme B, an appropriately substituted indanone (IIa) is arylated using a diaryliodonium halide ([R]₂IZ), wherein Z is halogen especially iodide or bromide, to give (IIc). Similarly, (IIb) is alkylated with R'Z to give (IIc) by an alternate route. Treatment of (IIc) with pyridine hydrochloride or aluminum chloride in an inert solvent produces the indanone (IId).

The indanone, (IId), is then treated with allyl bromide to yield the corresponding 5-allyl ether (IIe). Typically the allyl bromide is employed in excess; in fact it may serve as the reaction solvent. Other solvents, provided they are compatible with the desired course of reaction may be employed, for example, ethanol, dimethylformamide and the like. Typically the reaction is conducted in the presence of a base such as sodium alkoxide, potassium carbonate and the like at a temperature in the range of from about 25° to about 100°C. and is substantially complete in from about 0.5 to about 2 hours. The Claisen rearrangement to obtain the 4-allyl compound (IIf) is effected by continued heating of the reaction mixture at from about 100° to about 220°C. Alternately the 5-allyloxy species may be separated from the reaction mixture; dissolved in a solvent such as N,N-dimethylaniline, N,N-diethylaniline and the like; and heated at the reflux temperature of the solvent for 0.5 to 4 hours to yield (IIf). The indenofuran nucleus, (IIh), is obtained from the (IIf) species by treatment with a peracid such as m-chloroperbenzoic, peracetic acid and the like in a solvent such as methylene chloride, chloroform, acetic acid and the like at a temperature of from about 0°C. to the reflux temperature of the solvent wherein the epoxide (IIg), which is initially formed, cyclizes to (IIh). Oxidation of the resulting hydroxymethyl substituted indenofuran (IIh) yields the indenofurans of the present invention (II). Typically the oxidation is effected by oxidizing agents such as chromic acid, potassium permanganate and the like; the temperature of reaction is typically in the range of from about 0°C. to the reflux temperature of the solvent.

Scheme B is most suitable for the preparation of the saturated species of the present invention represented by structure II, above-depicted.

Scheme C is particularly suited for the preparation of the 1,2-unsaturated embodiments, (III); the saturated 1,2,7,8-tetrahydro embodiments are readily obtainable therefrom by reduction. Central to Scheme C is an appropriately 6,7-disubstituted benzofuran (or benzothiophene)-2-carboxylic acid (IIIa) and (IIIb), respectively.

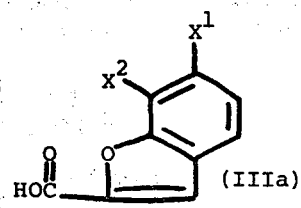

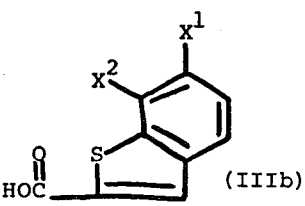

wherein $X^2$ and $X^1$ have previously been defined. Such benzofuran and benzothiophene compounds are known and available. See for example U.S. Pat. Nos. 3,627,785 (Dec. 14, 1971) and 3,651,094 (Mar. 21, 1972). Alternately such compounds may readily be prepared by known procedures. For example, the benzofuran of structure (IIIa) may readily be prepared from an appropriately 2,3-disubstituted phenol in reaction with malic acid in concentrated sulphuric acid to provide the corresponding disubstituted coumarin which upon bromination and subsequent treatment with potassium hydroxide in ethanol yields (IIIa).

Scheme C may be generally depicted in the following manner:

Scheme C

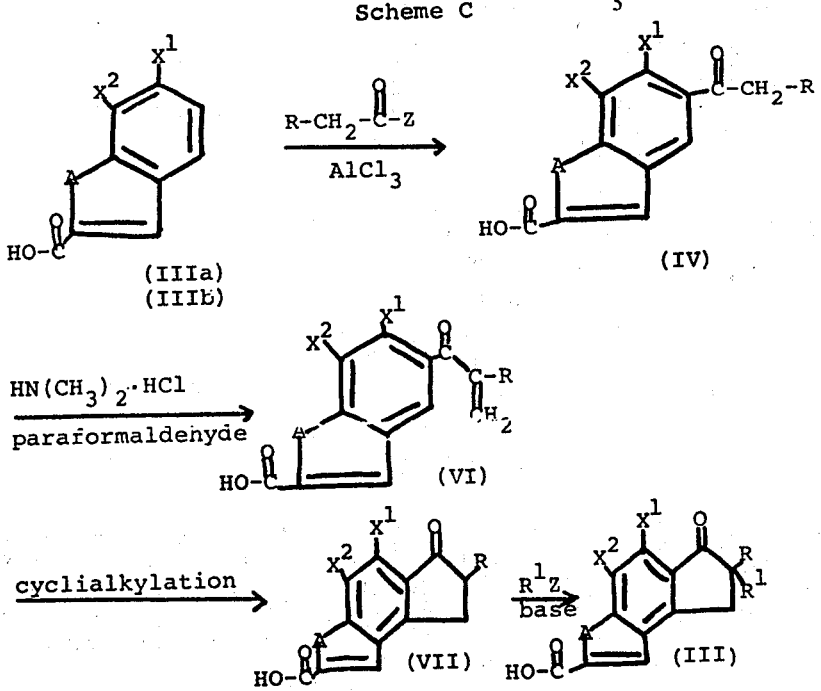

According to Scheme C, an appropriately substituted benzofuran (IIIa) (or benzothiophene)-2-carboxylic acid (IIIb) is reacted under Friedel-Crafts conditions with a carboxylic acid halide (or anhydride) of the formula:

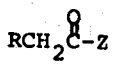

wherein R has previously been defined and Z is halogen such as chloro or bromo, to yield the corresponding 5-acyl species:

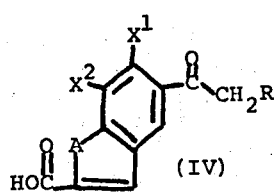

respectively, wherein A is oxygen or sulphur. Suitable catalysts for the reaction are aluminum chloride, tin (IV) chloride and the like. The reaction solvent and temperature are not critical inasmuch as any solvent which is inert to the acyl halide/benzofuran (benzothiophene) reactants may be employed. In this regard, suitable solvents include aliphatic and cycloaliphatic hydrocarbons such as heptane, cyclohexane, and the like; nitrohydrocarbons such as nitrobenzene and the like; and halogenated hydrocarbons such as carbon tetrachloride, methylene chloride, and the like. Typically the reaction is conducted at from 0°C. to the reflux temperature of the particular solvent employed.

The Friedel-Crafts product, (IV), is prepared for cyclialkylation to the ultimate indenofuran of this invention by the following method. A 2'-methylene derivative, (VI), is prepared via a Mannich intermediate, (V), by treating (IV) in paraformaldehyde in the presence of a secondary amine, such as dimethylamine hydrochloride, and the like:

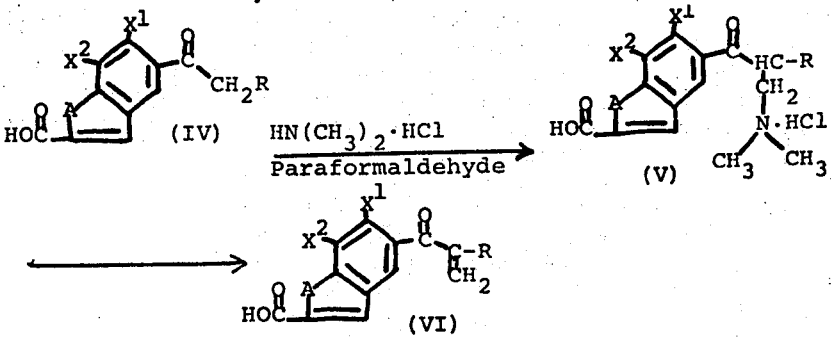

The 2'-methylene species (VI) is obtained from the Mannich intermediate (V) on treatment with aqueous sodium bicarbonate, sodium acetate or anhydrous dimethylformamide.

Cyclialkylation of (VI), thus prepared, yields the indenofurans of the present invention. The cyclialkylation is effected by treatment with a Lewis Acid such as concentrated sulphuric, polyphoshoric acid, boron trifluoride and the like at a temperature of from about 0°C. to about 60°C. The following equations illustrate this process:

(VI) cyclialkylation 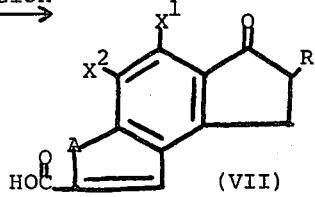

All embodiments of the present invention may be obtained from the above-described 1,2-unsaturated embodiments. 1,2-Dihydro embodiments are readily prepared by reduction with soium amalgam followed by oxidation of the resulting carbinol (which are also diuretic/saluretic, uricosuric and antihypertensives) to the desired keto form. The following equation generally illustrates this process:

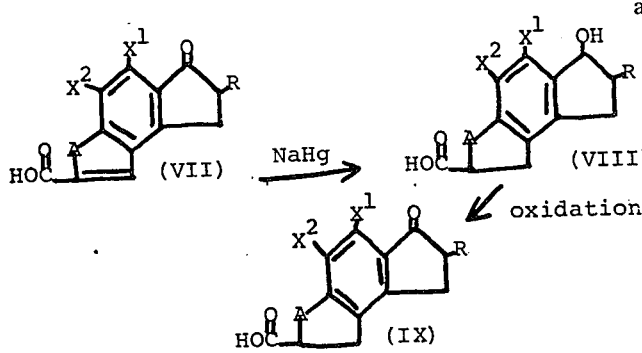

Typically the reduction is carried out in excess aqueous sodium bicarbonate solution, and typically the reaction is complete in from 2 to about 24 hours at 0° to about 25°C. Suitable oxidizing agents include chromic acid, potassium permanganate, and the like. Typically the oxidation is conducted in a solvent such as acetone, water and the like.

Finally the 7,7-disubstituted embodiments are conveniently prepared by alkylation of (VII) or (IX) according to the following generalized equation:

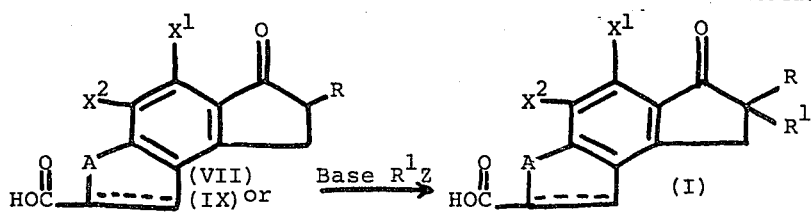

Wherein A, $R^1$, R, $X^2$, $X^1$ and the dashed line have been defined and Z is halogen such as bromo, chloro, iodo and the like. The above depicted alkylation is effected by first heating the 7-substituted indenofuran with a suitable base, for example, an alkali metal hydride such as sodium hydride and the like, or an alkali metal alkoxide, for example potassium tertiary butoxide and the like, other bases which may be employed include sodium amide, lithium amide and the like. The resulting carbanion is then treated with an alkylating agent $R^1Z$.

Any solvent which is inert or substantially inert to the reactants employed may be used. Suitable solvents include 1,2-dimethoxy ethane, tertiary butanol, benzene, dimethylformamide and the like. The reaction may be conducted at a temperature in the range of from about 25° to about 100°C.

As previously mentioned, the non-toxic, pharmacologically acceptable salts of the acids of Compound I are within the scope of this invention. These salts include those of alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals e.g., auminum, iron and zinc.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and the like. These salts ae particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of a indenofuran- or indenothiophene-2-carboxylic acid of this invention with an alcohol, for example, with a lower alkanol such as methanol or ethanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

The instant compounds herein disclosed contain one or more asymmetric carbon atoms (i.e. at positions 2 and 7 of the indenofuran ring). When this situation exists diasteriomers may be separated by methods well known to those skilled in the art and the optical antipodes may be separated by methods described below. This invention embraces, therefore, not only the racemic indeno[5,4-b]-furan-2-carboxylic acid diasteriomers but also their optically active antipodes.

Whether one or the other or both of the possible diasteriomers are formed is largely dependent upon the structure of (IIg) and upon the reaction conditions under which the furan ring is formed, i.e. the environment that prevails during the conversion of (IIg) to (IIh). Low reaction temperaturs (e.g. 0°C. to ambient temperatures) favor the formation of the α diasteriomer (see Example 1), while higher temperatures (e.g., 65°C. to 125°C. favor the formation of the β diasteriomer (see Example 2). If mixtures of the two diasteriomers are produced, they may be separated and identified by convential means, e.g., fractional crystallization or chromatography since they possess sufficiently different melting points and solubility properties.

Separation of the optical isomers of the racemic acids may be accomplished by forming a salt of the racemic mixture with an optically active base such as (+) or (−) amphetamine, (−)-cinchonidine, dehydroabietylamine, (+) or (−)-α-methylbenzylamine, (+) or (−)-α-(1-naphthyl)-ethylamine, brucine or strychnine and the like in a suitable solvent such as methanol, ethanol, 2-propanol, benzene, acetonitrile, nitromethane, acetone and the like. There is thus formed in the solution two diastereomeric salts one of which is usually more soluble in the solvent than the other. Repetitive crystallization of the crystalline salt generally affords a pure enantiomer. The optically pure indeno[5,4-b]furan-2-carboxylic acid is obtained by acidification of the salt with a mineral acid, extraction into ether, evaporation of the solvent and recrystallization of the optically pure antipode.

The other optically pure antipode may generally be obtained by using a different base to form the diastereomeric salt. It is of advantage to isolate the partially resolved acid from the filtrates of the purification of the one diatereomeric salt and to further purify this substance through the use of another optically active base.

Although diuretics are often life-saving because of the above beneficial therapeutic effects, most of them have the disadvantage of causing the excretion of appreciable amounts of potassium ions. When an excessive loss of potassium ions occurs a severe muscular weakness and feeling of extreme physical exhaustion results. The patient eliminates the unwanted sodium ions due to the action of the diuretic drugs but the undesired elimination of the potassium ions produces an imbalance that should not be allowed to persist.

This invention also involves co-administration of an indeno[5,4-b]furan with a pyrazinoylguanidine either in the form of a salt and/or as a mixture with a hydrochloride salt of a pyrazinoylguanidine, to thereby prevent the elimination of excessive amounts of potassium ions without altering or actually increasing the amount of sodium ions that are eliminated.

To achieve the beneficial results of this invention, the preferred pyrazinoylguanidine compound is N-amidino-3,5-diamino-6-chloropyrazinecarboxamide (amiloride) or its hydrochloride salt (amiloride hydrochloride) which is described in the literature and patented arts.

Another advantage of the N-amidino-3,5-diamino-6-chloropyrazinecarboxamide salts of the indeno[5,4-b]furan diuretics is their insolubility which makes the salts' gastrointestinal absorption slower and more gradual providing a chemical method of achieving the same effect as microencapsulation.

The examples which follow illustrate the indenofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

4,5-Dichloro-6-oxo-7-methyl-7-phenyl-1,2,7,8-tetrahydro-6H-indeno[5,4-b]furan-2-carboxylic acid (α-isomer)

Step A: 2',3'-Dichloro-4'-methoxyisobutyrophenone

A stirred mixture of 2,3-dichloroanisole (100 g., 0.565 mole) and isobutyryl chloride (66 g., 0.62 mole) in methylene chloride (400 ml.) is cooled to 5°C. and treated with aluminum cloride (83 g., 0.62 mole) during a one-hour period. The reaction mixture is allowed to warm to 25°C. and after 24 hours is poured into ice water (400 ml.) and hydrochloric acid (30 ml.). The organic phase is washed with 5% sodium hydroxide, water, dried over magnesium sulfate and distilled at reduced pressure affording 68 g. of 2',3'-dichloro-4'-methoxyisobutyrophenone which distills at 120°C–130°C./0.5 mm.

Elemental analysis for $C_{11}H_{12}Cl_2O_2$: Calc.: C, 53.46; H, 4.89; Found: C, 54.25; H, 5.07.

Step B: 2-Bromo-2',3'-dichloro-4'-methoxisobutyrophenone

A stirred solution of 2',3'-dichloro-4'-methoxyisobutyrophenone (45 g., 0.183 mole) in acetic acid (150 ml.) is treated during one-half hour with bromine (30 g., 0.187 mole). The reaction mixture is stirred 10 minutes, then poured into ice water (600 ml.) containing sodium bisulfite (2 g.). The 2-bromo-2',3'-dichloro-4'-methoxyisobutyrophenone which separates (48 g.) melts at 72°–73°C. after recrystallization from hexane.

Elemental analysis for $C_{11}H_{11}BrCl_2O_2$: Calc.: C, 40.52; H, 3.40; Found: C, 40.68; H, 3.38.

Step C: 2-Methylene-2',3'-dichloro-4'-methoxypropiophenone

A solution of 2-bromo-2',3'-dichloro-4'-methoxyisobutyrophenone (32 g., 0.1 mole) and anhydrous lithium bromide (17.4 g., 0.2 mole) in DMF (200 ml.) is stirred at 95°C. in an inert atmosphere for 3 hours and poured into ice water (500 ml.). The 2-methylene-2',3'-dichloro-4'-methoxypropiophenone which separates melts at 59°C. after recrystallization from petroleum ether.

Elemental analysis for $C_{11}H_{10}Cl_2O_3$: Calc.: C, 53.90; H, 4.11; Found: C, 53.72; H, 4.11.

Step D: 2-Methyl-5-methoxy-6,7-dichloro-1-indanone

A solution of 2-methylene-2',3'-dichloro-4'-methoxypropiophenone (40 g., 0.163 mole) in concentrated sulfuric acid (75 ml.) is allowed to stand at 25°C. for 24 hours and then is slowly poured into vigorously stirred ice water (500 ml.). The 2-methyl-5-methoxy-6,7-dichloro-1-indanone which separate (40 g.) melts at 129°C. after recrystallization from methylcyclohexane.

Elemental analysis for $C_{11}H_{10}Cl_2O_2$: Calc.: C, 53.90; H, 4.11; Found: C, 53.84; H, 4.00.

Step E: 2-Methyl-2-phenyl-5-methoxy-6,7-dichloro-1-indanone

Potassium tert-butoxide (8.42 g., 0.075 mole) dissolved in tert-butanol (300 ml.) is added to a refluxing solution of 2-methyl-5-methoxy-6,7-dichloro-1-indanone (12.26 g., 0.05 mole), refluxing is continued for two hours, then a suspension of diphenyliodonium chloride (19.0 g., 0.06 mole) in tert-butanol (1 l.) is added and refluxing is continued for two hours. The reaction mixture is cooled to 25°C., 300 ml. water added, and the mixture concentrated to dryness in vacuo to give 4.97 g. of 2-methyl-2-phenyl-5-methoxy-6,7-dichloro-1-indanone which melts at 161°–163°C. after crystallization from benzene:cyclohexane, 1:2.

Elemental analysis for $C_{17}H_{14}Cl_2O_2$: Calc.: C, 63.57; H, 4.39; Found: C, 63.24; H, 4.68.

Step F: 2-Methyl-2-phenyl-5hydroxy-6,7-dichloro-1-indanone

A stirred mixture of 2-methyl-2-phenyl-5-methoxy-6,7-dichloro-1-indanone (4.94 g., 0.015 mole) and pyridine hydrochloride (50 g.) is heated at 175°C. for 1 hour, then poured into water (500 ml.). The 2-methyl-2-phenyl-5-hydroxy-6,7-dichloro-1-indanone which separates (2.05 g.) melts at 194°–196°C. after recrystallization from ethanol:water, 2;1.

Elemental analysis for $C_{16}H_{12}Cl_2O_2$: Calc.: C, 62.56; H, 3.94; Found: C, 62.60; H, 4.11.

Step G: 2-Methyl-2-phenyl-5-allyloxy-6,7-dichloro-1-indanone

A stirred mixture of 2-methyl-2-phenyl-5-hydroxy-6,7-dichloro-1-indanone (15 g., 0.049 mole), potassium carbonate (7.4 g., 0.053 mole) and allylbromide (6.58 g., 0.054 mole) in dimethylformamide (80 ml.) is heated at 55°C. for 1 hour then poured into water (400 ml.). The 2-methyl-2-phenyl-5-allyloxy-6,7-dichloro-1-indanone which separates melts at 105°C. after recrystallization from cyclohexane.

Elemental analysis for $C_{19}H_{16}Cl_2O_2$: Calc.: C, 65.72; H, 4.64; Found: C, 66.14; H, 4.65.

Step H: 2-Methyl-2-phenyl-4-allyl-5-hydroxy-6,7-dichloro-1-indanone

A mixture of 2-methyl-2-phenyl-5-allyloxy-6,7-dichloro-1-indanone (12.5 g., 0.036 mole) in N,N-diethylaniline (120 ml.) is refluxed for one and one-half hours then poured into excess cold dilute hydrochloric acid. The product is extracted into ether, washed with water and dried over anhydrous magnesium sulfate. Evaporation of the ether affords 2-methyl-2-phenyl-4-allyl-5-hydroxy-6,7-dichloro-1-indanone which melts at 125°C. after crystallization from butyl chloride.

Elemental analysis for $C_{19}H_{16}Cl_2O_2$: Calc.: C, 65.72; H, 4.64; Found: C, 65.65; H, 4.74.

Step I: 4,5-Dichloro-2-hydroxymethyl-6-oxo-7-methyl-7-phenyl-1,2,7,8-tetrahydro-6H-indeno[5,4-b]-furan (α-isomer)

To a solution of 2-methyl-2-phenyl-4-allyl-5-hydroxy-6,7-dichloro-1-indanone (8.2 g., 0.024 mole) in dichloromethane (80 ml.) is added sodium acetate (150 mg.) and 40% peracetic acid (6 ml.). The reaction is stirred at 25°C. for 12 days during which time two 1 ml. portions of 40% peracetic acid are added at four day intervals. The reaction mixture is washed with water, aqueous sodium bicarbonate and brine. The solvent is distilled at reduced pressure and the residual oil is heated at 120°C. for 20 minutes affording 4,5-dichloro-2-hydroxymethyl-6-oxo-7-phenyl-1,2,7,8-tetrahydro-6H-indeno-[5,4-b]-furan (α-isomer) which is used in the next step without further purification.

Step J: 4,5-Dichloro-6-oxo-7-methyl-7-phenyl-1,2,7,8-tetrahydro-6H-indeno-[5,4-b]-furan-2-carboxylic acid (α-isomer)

To the compound, obtained by the process described in Step I, dissolved in acetone (300 ml.) is added an oxidizing solution comprised of chromium trioxide (7 g.) dissolved in a mixture of water (50 ml.) and concentrated sulfuric acid (6.2 ml.). The reaction is stirred for 18 hours at 25°C. The acetone solution containing the product is decanted from precipitated salts, diluted with water (300 ml.), treated with sodium sulfite (0.5 g.) distilled at reduced pressure to a volume of 300 ml., extracted with ether which is washed with water and dried over anhydrous magnesium sulfate to give 4,5-dichloro-6-oxo-7-methyl-7-phenyl-1,2,7,8-tetrahydro-6H-indeno-[5,4-b]-furan-2-carboxylic acid (α-isomer) which melts at 244°C. after recrystallization from nitromethane.

Elemental analysis for $C_{19}H_{14}Cl_2O_4$; Calc.: C, 60.49; H, 3.74; Cl, 18.80; Found: C, 59.66; H, 4.01; Cl, 19.01.

EXAMPLE 2

4,5-Dichloro-6-oxo-7-methyl-7-phenyl-1,2,7,8-tetrahydro-6H-indeno[5,4-b]-furan-2-carboxylic acid (β-isomer)

Step A: 2',3'-Dichloro-4'-methoxy-2-phenylacetophenone

Aluminum chloride (395 g.) is added portionwise to a stirred solution of 2,3-dichloroanisole (500 g.) and phenylacetyl chloride (392 ml.) in carbon disulfide (1200 ml.) with cooling to 5°C. in an ice-water bath. After the addition, the reaction mixture is allowed to warm to room temperature, whereupon it forms a solid mass. After standing at 20°–25°C. overnight, the reaction vessel is flushed with nitrogen for 15 minutes, and crushed ice (about 2 kg.) and 12N HCl (400 ml.) are slowly added alternately with cooling in an ice bath. The pale yellow gummy solid that precipitates is collected by suction filtration on a sintered glass funnel to remove water as well as carbon disulfide. The solid product is washed well with water and sucked dry. To remove any persistent carbon disulfide, the product is triturated with hexane and again collected by filtration. Yield after drying in a steam oven at 70°C. for 18 hours is 803.5 g. (98%), mp 125°–127°C. A sample recrystallized from benzene-cyclohexane (2:1) melts at 128°–129°C.

Elemental analysis for $C_{15}H_{12}Cl_2O_2$: Calc.: C, 61.04; H, 4.10; Found: C, 61.46; H, 4.11.

Step B: 2',3'-Dichloro-4'-methoxy-2-phenylacrylophenone

2',3'-Dichloro-4'-methoxy-2-phenylacetophenone (300 g.) is suspended in 1000 ml. of N,N,N,N-tetramethylmethanediamine at 25°C. under nitrogen, and acetic anhydride (1000 ml.) is added dropwise. The reaction mixture is maintained below 40°C. by cooling in an ice-water bath and regulating the rate of anhydride addition. The reaction mixture is left at 25°C. for 1 hour then slowly added to crushed ice-water (8 liters) with stirring. The white solid precipitate is collected by suction filtration, washed with water, and air-dried at 25°C. for 2 days. Yield: 310.5 g. (99%), mp 87°–89°C. A sample recrystallized from benzene-hexane melts at 87°–89°C.

Elemental analysis for $C_{16}H_{12}Cl_2O_2$: Calc.: C, 62.56; H, 3.94; Found: C, 62.67; H, 4.04.

Step C: 2-Phenyl-5-methoxy-6,7-dichloro-1-indanone

2',3'-Dichloro-4'-methoxy-2-phenylacrylophenone (160 g.) dissolved in dichloromethane (4 liters) is added dropwise to a mixture of 12N sulfuric acid (2 liters) and dichloromethane (2 liters) at <5°C. over a 3-hour period. The reaction mixture is stirred for an additional 30 minutes then poured slowly onto crushed ice. The dichloromethane layer is separated, washed with saturated sodium chloride solution, then dried over anhydrous magnesium sulfate. The solvent is removed under reduced pressure leaving a light tan solid residue. On drying in a steam oven at 70°C., 120.5 g. of product (75%) is obtained, mp 187°–192°C. A sample recrystallized from benzene-cyclohexane (2:1) melts at 193°–195°C.

Elemental analysis for $C_{16}H_{12}Cl_2O_2$: Calc.: C, 62.56; H, 3.94; Found: C, 62.84; H, 4.00.

Step D: 2-Methyl-2-phenyl-5-methoxy-6,7-dichloro-1-indanone

2-Phenyl-5-methoxy-6,7-dichloro-1-indanone, 50.84 g. is dissolved in 700 ml. dry DMF and 700 ml. benzene in a 3-liter flask equipped with a nitrogen inlet, air condenser and hopper for $NaOCH_3$. The reaction mixture is cooled in ice-water and 103 ml. of iodomethane is added. $NaOCH_3$, 13.5 g., is added portion wise from the hopper over ¾ of an hour. After stirring for ½ hour in an ice-water bath, the reaction mixture is added to water, (4 liters), and extracted with benzene. The benzene layer is separated dried over molecular sieves and concentrated to dryness to give 2-methyl-2-phenyl-5-methoxy-6,7-dichloro-1-indanone, mp 164°–5°C. after recrystallization from benzene-cyclohexane, 1:2.

Elemental analysis for $C_{17}H_{14}Cl_2O_2$: Calc.: C, 63.57; H, 4.39; Found: C, 63.24; H, 4.68.

Step E: 2-Methyl-2-phenyl-5-hydroxy-6,7-dichloro-1-indanone

A stirred mixture of 2-methyl-2-phenyl-5-methoxy-6,7-dichloro-1-indanone (4.94 g., 0.015 mole) and pyridine hydrochloride (50 g.) is heated at 175°C. for 1 hour, then poured into water (500 ml.). The 2-methyl-2-phenyl-5-hydroxy-6,7-dichloro-1-indanone which separates (2.05 g.) melts at 194°–196°C. after recrystallization from ethanol:water, 2:1.

Elemental analysis for $C_{16}H_{12}Cl_2O_2$: Calc.: C, 62.56; H, 3.94; Found: C, 62.60; H, 4.11.

Step F: 2-Methyl-2-phenyl-5-allyloxy-6,7-dichloro-1-indanone

A stirred mixture of 2-methyl-2-phenyl-5-hydroxy-6,7-dichloro-1-indanone (15 g., 0.049 mole), potassium carbonate (7.4 g., 0.053 mole) and allylbromide (6.58 g., 0.054 mole) in dimethylformamide (80 ml.) is heated at 55°C. for 1 hour then poured into water (400 ml.). The 2-methyl-2-phenyl-5-allyloxy-6,7-dichloro-1-indanone which separates melts at 105°C. after recrystallization from cyclohexane.

Elemental analysis for $C_{19}H_{16}Cl_2O_2$: Calc.: C, 65.72; H, 4.64; Found: C, 66.14; H, 4.65.

Step G: 2-Methyl-2-phenyl-4-allyl-5-hydroxy-6,7-dichloro-1-indanone

A mixture of 2-methyl-2-phenyl-5-allyloxy-6,7-dichloro-1-indanone (12.5 g., 0.036 mole) in N,N-diethylaniline (120 ml.) is refluxed for one and one-half hours then poured into excess cold dilute hydrochloric acid. The product is extracted into ether, washed with water and dried over anhydrous magnesium sulfate. Evaporation of the ether affords 2-methyl-2-phenyl-4-allyl-5-hydroxy-6,7-dichloro-1-indanone which melts at 125°C. after crystallization from butyl chloride.

Elemental analysis for $C_{19}H_{16}C_{12}O_2$: Calc.: C, 65.72; H, 4.64; Found: C, 65.65; H, 4.74.

Step H: 4,5-Dichloro-2-hydroxymethyl-6-oxo-7-methyl-7-phenyl-1,2,7,8-tetrahydro-6H-indeno[5,4-b]furan (β-isomer)

To a solution of 2-methyl-2-phenyl-4-allyl-5-hydroxy-6,7-dichloro-1-indanone (1.73 g., 0.005 mole) in methylene chloride (30 ml.) is added m-chloroperbenzoic acid (1.03 g., 0.006 mole) and 4,4'-thiobis-6-tert-butyl-m-cresol (10 mg.). The reaction is heated at reflux for 5 hours then cooled to 25°C. The m-chlorobenzoic acid which separates is filtered and the solution is washed with water, aqueous sodium bicarbonate and brine. The solvent is distilled at reduced pressure and the residual oil is heated at 120°C. for twenty minutes affording 4,5-dichloro-2-hydroxymethyl-6-oxo-7-methyl-7-phenyl-1,2,7,8-tetrahydro-6H-indeno[5,4-b]-furan (β-isomer) which is used in the next step without further purification.

Step I: 4,5-Dichloro-6-oxo-7-methyl-7-phenyl-1,2,7,8-tetrahydro-6H-indeno[5,4-b]-furan-2-carboxylic acid (β-isomer)

To the compound, obtained by the process described in Step H, dissolved in acetone (60 ml.) is added an oxidizing solution comprised of chromium trioxide (1.4 g.) dissolved in a mixture of water (10 ml.) and concentrated sulfuric acid (1.24 ml.). The reaction is stirred for 18 hours at 25°C. The acetone solution containing the product is decanted from precipitated salts, diluted with water (60 ml.), treated with sodium sulfite (0.1 g.) distilled at reduced pressure to a volume of 60 ml., extracted with ether which is washed with water and dried over anhydrous magnesium sulfate to give 4,5-dichloro-6-oxo-7-methyl-7-phenyl-1,2,7,8-tetrahydro-6H-indeno-[5,4-b]furan-2-carboxylic acid (β-isomer) which melts at 188°C. after recrystallization from nitromethane and contains 1/6 mole nitromethane as a solvate.

Elemental analysis for $C_{19}H_{14}Cl_2O_4(+1/6\ CH_3NO_2)$: Calc.: C, 59.27; H, 3.77; N, 0.6; Found: C, 59.00; H, 3.72; N, 0.24.

EXAMPLE 3

Where in Example 1, Step A, there is substituted for the 2,3-dichloroanisole an equivalent amount of 2-chloro-3-methylanisole, 2,3-dimethylanisole, or 2-methyl-3-chloroanisole, respectively, and Steps B through J are employed as described there is obtained: 4-chloro-6-oxo-5,7-dimethyl-7-phenyl-1,2,7,8-tetrahydro-6H-indeno-[5,4-b]furan-2-carboxylic acid (α-isomer); 6-oxo-4,5,7-trimethyl-7-phenyl-1,2,7,8-tetrahydro-6H-indeno[5,4-b]-furan-2-carboxylic acid (α-isomer); and 5-chloro-6-oxo-4,7-dimethyl-7-phenyl-1,2,7,8-tetrahydro-6H-indeno[5,4-b]furan-2-carboxylic acid (α-isomer), respectively.

EXAMPLE 4

Where in Example 2, there is substituted for the phenylacetyl chloride of Step A an equivalent amount of p-methylphenylacetyl chloride, m-methylphenylacetyl chloride, o- or p-chlorophenylacetyl chloride, p-furorophenylacetyl chloride, and Steps B through J of Example 1 are employed as therein described there is obtained respectively: 4,5-Dichloro-6-oxo-7-methyl-7-(p-methylphenyl)-1,2,7,8-tetrahydro-6H-indeno[5,4-b]-furan-2-carboxylic acid (α-isomer); 4,5-dichloro-6-oxo-7-methyl-7-(m-methylphenyl)-1,2,7,8-tetrahydro-6H-indeno[5,4-b]-furan-2-carboxylic acid (α-isomer); 4,5-dichloro-6-oxo-7-methyl-7-(o- or p-chlorophenyl)-1,2,7,8-tetrahydro-6H-indeno[5,4-b]-furan-2-carboxylic acid (α-isomer); 4,5-dichloro-6-oxo-7-methyl-7-(p-fluorophenyl)-1,2,7,8-tetrahydro-6H-indeno[5,4-b]-furan-2-carboxylic acid (α-isomer).

EXAMPLE 5

Where in Example 1, Step A, there is substituted for the 2,3-dichloroanisole an equivalent amount of 2-chloro-3-methylanisole, 2,3-dimethylanisole, or 2-methyl-3-chloroanisole, respectively, and Steps B through I of Example 2 are employed as described there is obtained: 4-chloro-6-oxo-5,7-dimethyl-7-phenyl-1,2,7,8-tetrahydro-6H-indeno[5,4-b]furan-2-carboxylic acid (β-isomer); 6-oxo-4,5,7-trimethyl-7-phenyl-1,2,7,8-tetrahydro-6H-indeno-[5,4-b]furan-2-carboxylic acid (β-isomer); and 5-chloro-6-oxo-4,7-dimethyl-7-phenyl-1,2,7,8-tetrahydro-6H-indeno[5,4-b]furan-2-carboxylic acid (β-isomer), respectively.

EXAMPLE 6

Where in Example 2, there is substituted for the phenylacetyl chloride of Step A an equivalent amount of p-methylphenylacetyl chloride, m-methylphenylacetyl chloride, o- or p-chlorophenylacetyl chloride, p-fluorophenylacetyl chloride, and Steps B through I of Example 2 are employed as therein described there is obtained respectively: 4,5-Dichloro-6-oxo-7-methyl-7-(p-methylphenyl)-1,2,7,8-tetrahydro-6H-indeno[5,4-b]-furan-2-carboxylic acid (β-isomer); 4,5-dichloro-6-oxo-7-methyl-7-(m-methylphenyl)-1,2,7,8-tetrahydro-6H-indeno[5,4-b]-furan-2-carboxylic acid (β-isomer); 4,5-dichloro-6-oxo-7-methyl-7-(o- or p-chlorophenyl)-1,2,7,8-tetrahydro-6H-indeno[5,4-b]-furan-2-carboxylic acid (β-isomer); 4,5-dichloro-6-oxo-7-methyl-7-(p-fluorophenyl)-1,2,7,8-tetrahydro-6H-indeno[5,4-b]-furan-2-carboxylic acid (β-isomer).

EXAMPLE 7

4,5-Dichloro-6-oxo-7-methyl-7-thienyl-1,2,7,8-tetrahydro-6H-indeno[5,4-b]-furan-2-carboxylic acid (α-isomer)

Where in Example 1, Step E there is substituted for the diphenyliodonium chloride an equivalent amount of dithienyliodonium chloride and Steps F through J are employed as described there is obtained: 4,5-dichloro-6-oxo-7-methyl-7-thienyl-1,2,7,8-tetrahydro-6H-indeno[5,4-b]-furan-2-carboxylic acid(α-isomer).

EXAMPLE 8

4,5-Dichloro-6-oxo-7-methyl-7-thienyl-1,2,7,8-tetrahydro-6H-indeno[5,4-b]-furan-2-carboxylic acid(β-isomer)

Where in Example 1, Step E there is substituted for the diphenyliodonium chloride an equivalent amount of dithienyliodonium chloride and Steps F through I of Example 2 are employed as described there is obtained: 4,5-dichloro-6-oxo-7-methyl-7-thienyl-1,2,7,8-tetrahydro-6H-indeno[5,4-b]-furan-2-carboxylic acid (β-isomer).

The Examples above are illustrative only and it will be apparent to those having ordinary skill in the art that the products enumerated in Table I may be prepared in an analogous manner by substituting the appropriate starting materials for those set forth in the Examples.

Table I

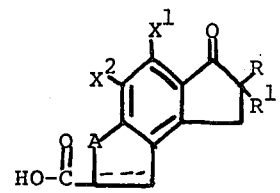

| Example | A | R | R¹ | X¹ | X² |
|---|---|---|---|---|---|
| 9 | S | Ph | CH₃ | CH₃ | CH₃ |
| 10 | S | Ph | CH₃ | Cl | Cl |
| 11 | S | p-ClPh | CH₃ | Cl | Cl |
| 12 | S | thienyl | CH₃ | Cl | Cl |

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 2, 5, 10, 25, 100, 150, and 250 of the active ingredient for the symptomatic adjustment of the dosage to the individual being treated.

A suitable unit dosage form of the product of this invention can be administered by mixing 50 mg. of an indenofuran or a suitable salt, ester or amide derivative thereof of the present invention with 149 mg. of lactose and 1 mg. of magnesium stearate and placing the 200 mg. mixture into a No. 1 gelatin capsule. Similarly by employing more of the active ingredient and less lactose, other dosage forms can be put up in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

An effective amount of the product is ordinarily supplied at a dosage level of from about 0.1 mg. to about 10 mg./kg. of body weight of the patient. Preferably the range is from about 0.3 mg. to about 1.0 mg./kg. with a most preferred dose being about 0.35 mg./kg. of body weight.

It is also within the scope of this invention to combine two or more of the compounds of this invention into a unit dosage form or to combine one or more of the compounds of this invention with other known diuretics and saluretics or with other desired therapeutic and/or nutritive agents in dosage unit form.

The present invention embraces such compositions for oral administration wherein the potassium conserving diuretic, N-amidino-3,5-diamino-6-chloropyrazinecarboxamide hydrochloride, hereinafter referred to as amiloride hydrochloride, is present as a physical mixture in combination with the indenofurans of the present invention. The present invention embraces compositions wherein the molar ratio of the indenofuran to amiloride hydrochloride ranges from about 50:1 to 1:1. The preferred ratios of the indenofurans to amiloride hydrochloride ranges from 25:1 to 1:1. For the case wherein the indenofuran is the α- or β-isomer of 4,5-dichloro-6-oxo-7-methyl-7-phenyl-1,2,7,8-tetrahydro-6H-indeno[5,4-b]furan-2-carboxylic acid the preferred absolute weights and weight ratios corresponding to the above recited molar ratio are set forth in Table 2.

If, in Examples 13 and 14, one of the other mentioned indenofuran diuretics is substituted for 4,5-dichloro-6-oxo-7-methyl-7-phenyl-1,2,7,8-tetrahydro-6H-indeno[5,4-b]furan-7-carboxylic acid, it would be used in a greater or lesser amount depending upon its diuretic activity.

Similar dry-filled capsules are prepared by replacing the active ingredient of the above example by the sodium, diethanolamine, and triethanolamine salt thereof, respectively.

The following example is included to illustrate the preparation of a representative combined dosage form containing a mixture of an indenofuran and amiloride hydrochloride.

TABLE 1

| Absolute Weight (mg.) of Components | | Weight Ratio | | Mole Rato | |
|---|---|---|---|---|---|
| α- or β-isomer of 4,5-dichloro-6-oxo-7-methyl-7-phenyl-1,2,7,8-tetrahydro-6H-indeno[5,4-b]-furan-2-carboxylic acid | Amiloride /Hydrochloride | α- or β-isomer of 4,5-dichloro-6-oxo-7-methyl-7-phenyl-1,2,7,8-tetrahydro-6H-indeno[5,4-b]-furan-2-carboxylic acid | /Amiloride /Hydrochloride | α- or β-isomer of 4,5-dichloro-6-oxo-7-methyl-7-phenyl-1,2,7,8-tetrahydro-6H-indeno[5,4-b]-furan-2-carboxylic acid | /Amiloride /Hydrochloride |
| 200 | 5 | 40/1 | | 28/1 | |
| 40 | 25 | 1.6/1 | | 1.1/1 | |
| 20 | 5 | 4/1 | | 2.8/1 | |
| 10 | 5 | 2/1 | | 1.4/1 | |

The following examples are included to illustrate the preparation of representative dosage forms:

EXAMPLE 13

Dry-filled capsules containing 50 mg. of active ingredient per capsule

| | Per Capsule |
|---|---|
| 4,5-Dichloro-6-oxo-7-methyl-7-phenyl-1,2,7,8-tetrahydro-6H-indeno[5,4-b]-furan-2-carboxylic acid(α-isomer) | 50 mg. |
| Lactose | 149 mg. |
| Magnesium stearate | 1 mg. |
| Capsule (Size No. 1) | 200 mg. |

Similar dry-filled capsules are prepared by replacing the active ingredient of the above example by the sodium, diethanolamine, and triethanolamine salt thereof, respectively.

EXAMPLE 14

Dry-filled capsules containing 20 mg. of active ingredient

| | Per Capsule |
|---|---|
| 4,5-Dichloro-6-oxo-7-methyl-7-phenyl-1,2,7,8-tetrahydro-6H-indeno[5,4-b]-furan-2-carboxylic acid(β-isomer) | 20 mg. |
| Lactose | 179 mg. |
| Magnesium stearate | 1 mg. |
| Capsule (Size No. 1) | 200 mg. |

The 4,5-dichloro-6-oxo-7-methyl-7-phenyl-1,2,7,8-tetrahydro-6H-indeno[5,4-b]furan-2-carboxylic acid-(α-isomer) is reduced to a No. 60 powder and then lactose and magnesium stearate are passed through a No. 60 bolting cloth onto the powder and the combined ingredients admixed for ten minutes and then filled into a No. 1 dry gelatin capsule.

Similar dry-filled capsules are prepared by replacing the indenofuran of Examples 13 and 14 by any of the other indenofuran compounds recited in this invention.

EXAMPLE 15

Combined dosage form in dry-filled capsule

| | Per Capsule |
|---|---|
| 4,5-Dichloro-6-oxo-7-methyl-7-phenyl-1,2,7,8-tetrahydro-6H-indeno[5,4-b]-furan-2-carboxylic acid(α-isomer) | 10 mg. |
| N-Amidino-3,5-diamino-6-chloro-pyrazinecarboxamide hydrochloride | 5 mg. |
| Lactose | 184 mg. |
| Magnesium stearate | 1 mg. |
| Capsule (Size No. 1) | 200 mg. |

The 4,5-dichloro-6-oxo-7-methyl-7-phenyl-1,2,7,8-tetrahydro-6H-indeno[5,4-b]furan-2-carboxylic acid-(α-isomer) and N-amidino-6-chloropyrazinecarboxamide hydrochloride are mixed and reduced to a No. 60 powder and then lactose and magnesium stearate are passed through a No. 60 bolting cloth onto the powder and the combined ingredients admixed for ten minutes and then filled into a No. 1 dry gelatin capsule.

Similar combined dosage form dry-filled capsules are prepared by replacing the indenofuran ingredient of Example 15 by any of the other indenofuran compounds recited in this invention. If, in Example 15 one of the other mentioned indenofuran diuretics is substituted for 4,5-dichloro-6-oxo-7-methyl-7-phenyl-1,2,7,8-tetrahydro-6H-indeno[5,4-b]furan-2-carboxylic acid (α-isomer), it would be used in a greater or lesser amount depending upon its known relative diuretic activity with respect to the latter.

It will be apparent from the foregoing description that the indenofurans of this invention constitute a valuable class of compounds which have not been prepared heretofore. One skilled in the art will also appreciate that the processes disclosed in the above examples are merely illustrative and are capable of nonsubstantive modification without departing from the intended scope of the present invention as claimed.

What is claimed is:

1. A compound having the formula:

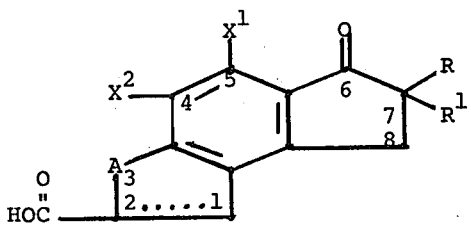

wherein the dotted line indicates 1,2-saturated or unsaturated embodiments; A is oxygen or sulfur; R is phenyl, substituted phenyl wherein the substituent is lower alkyl or halo, thienyl or substituted thienyl wherein the substituent is lower alkyl or halo; $R^1$ is lower alkyl; $X^1$ is lower alkyl or halo; $X^2$ is hydrogen, lower alkyl or halo; and the non-toxic pharmacologically acceptable salt, lower alkyl ester and mono and di lower alkyl, piperidino and morpholino amide derivatives thereof.

2. A compound according to claim 1 wherein the 1,2-position is unsaturated and A is oxygen.

3. The compound of claim 1 wherein the 1,2-position is saturated; A is oxygen; R is phenyl, chlorophenyl or thienyl; $R^1$ is methyl; $X^1$ is chloro or methyl; $X^2$ is hydrogen, chloro or methyl; and the non-toxic pharmaceutically acceptable salt, lower alkyl ester and mono and di lower alkyl, piperidino and morpholino amide derivatives thereof.

4. The compound of claim 3 which is 4,5-di-chloro-6-oxo-7-methyl-7-phenyl-1,2,7,8-tetrahydro-6H-indeno[5,4-b]furan-2-carboxylic acid and its nontoxic pharmaceutically acceptable salt, ester and amide derivatives.

5. The compound of claim 4 which is the α-diasteriomer of 4,5-dichloro-6-oxo-7-methyl-7-phenyl-1,2,7,8-tetrahydro-6H-indeno[5,4-b]furan-2-carboxylic acid.

6. The compound of claim 4 which is the β-diasteriomer of 4,5-dichloro-6-oxo-7-methyl-7-phenyl-1,2,7,8-tetrahydro-6H-indeno[5,4-b]furan-2-carboxylic acid.

7. The compound of claim 3 which is 4,5-dichloro-6-oxo-7-methyl-7-(p-chlorophenyl)-1,2,7,8-tetrahydro-6H-indeno[5,4-b]furan-2-carboxylic acid and its non-toxic pharmaceutically acceptable salt, ester and amide derivatives.

8. The compound of claim 3 which is 4,5-dichloro-6-oxo-7-methyl-7-thienyl-1,2,7,8-tetrahydro-6H-indeno[5,4-b]furan-2-carboxylic acid and its nontoxic pharmaceutically acceptable salt, ester and amide derivatives.

9. A pharmaceutical composition useful for the treatment of edema associated with hypertension comprising an effective amount of an indenofuran or indenothiophene compound of the formula:

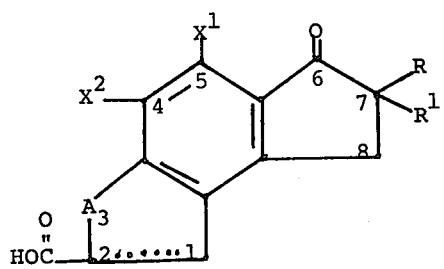

wherein the dotted line indicates 1,2-saturated or unsaturated embodiments; A is oxygen or sulfur; R is phenyl, substituted phenyl wherein the substituent is lower alkyl or halo, thienyl or substituted thienyl wherein the substituent is lower alkyl or halo; $R^1$ is lower alkyl; $X^1$ is lower alkyl or halo; $X^2$ is hydrogen, lower alkyl or halo; and the non-toxic, pharmacologically acceptable salt, lower alkyl ester and mono and di lower alkyl, piperidino and morpholino amide derivatives thereof; and a pharmaceutically acceptable carrier.

10. A composition useful for the treatment of edema associated with hypertension comprising an effective amount of an indenofuran or indenothiophene compound of the formula:

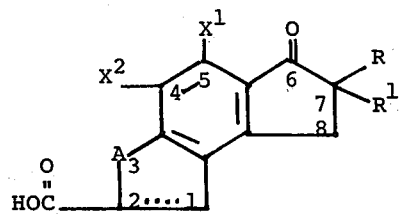

wherein the dotted line indicates 1,2-saturated or unsaturated embodiments; A is oxygen or sulfur; R is phenyl, substituted phenyl wherein the substituents is lower alkyl or halo, thienyl or substituted thienyl wherein the substituent is lower alkyl or halo; $R^1$ is lower alkyl; $X^1$ is lower alkyl or halo; $X^2$ is hydrogen, lower alkyl or halo; and the non-toxic, pharmacologically acceptable salt, lower alkyl ester and mono and di lower alkyl, piperidino and morpholino amide derivatives thereof and N-amidino-3,5-diamino-6-chloropyrazinecarboxamide hydrochloride wherein the mole ratio of the indenofuran or indenothiophene compound to N-amidino-3,5-diamino-6-chloropyrazinecarboxamide hydrochloride ranges from about 50:1 to 1:1.

11. A composition useful for the treatment of edema associated with hypertension comprising an effective amount of an indenofuran or indenothiophene compound of the formula:

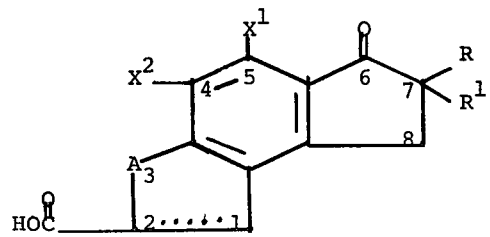

wherein the dotted line indicates 1,2-saturated or unsaturated embodiments; A is oxygen or sulfur; R is phenyl, substituted phenyl wherein the substituent is lower alkyl or halo, thienyl or substituted thienyl wherein the substituent is lower alkyl or halo; $R^1$ is lower alkyl having 1 to 6 carbon atoms; $X^1$ is lower alkyl or halo; $X^2$ is hydrogen, lower alkyl or halo; and the non-toxic, pharmacologically acceptable salt, lower alkyl ester and mono and di lower alkyl, piperidino and morpholino amide derivatives thereof and N-amidino-3,5-diamino-6-chloropyrazinecarboxamide hydrochloride wherein the mole ratio of the indenofuran or indenothiophene compound to N-amidino-3,5-diamino-6-chloropyrazinecarboxamide hydrochloride ranges from about 25:1 to 1:1.

12. A method of treatment of edema associated with hypertension in a patient in need of said treatment comprising the oral administration of a therapeutically effective amount in unitary dosage form of a compound having the formula:

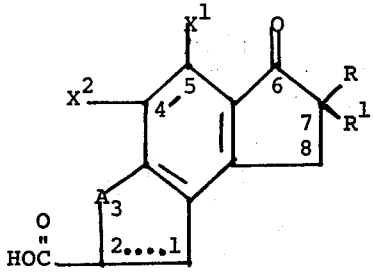

wherein the dotted line indicates 1,2-saturated or unsaturated embodiments; A is oxygen or sulfur; R is phenyl, substituted phenyl wherein the substituent is lower alkyl or halo, thienyl or substituted thienyl wherein the substituent is lower alkyl or halo; $R^1$ is lower alkyl; $X^1$ is lower alkyl or halo; $X^2$ is hydrogen, lower alkyl or halo; and the non-toxic, pharmacologically acceptable salt, lower alkyl ester and mono and di lower alkyl, piperidino and morpholino amide derivatives thereof.

13. A method of treatment of edema associated with hypertension in a patient in need of said treatment comprising the oral administration of a therapeutically effective amount in a combination dosage form of a composition comprising an indenofuran or indenothiophene of the formula:

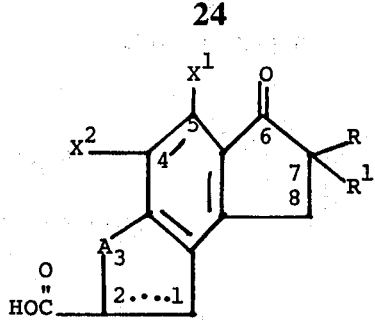

wherein the dotted line indicates 1,2-saturated or unsaturated embodiments; A is oxygen or sulfur; R is phenyl, substituted phenyl wherein the substituent is lower alkyl or halo, thienyl or substituted thienyl wherein the substituent is lower alkyl or halo; $R^1$ is lower alkyl having 1 to 6 carbon atoms; $X^1$ is lower alkyl or halo; $X^2$ is hydrogen, lower alkyl or halo; and the non-toxic, pharmacologically acceptable salt lower alkyl ester and mono and di lower alkyl, piperidino and morpholino amide derivatives thereof and N-amidino-3,5-diamino-6-chloropyrazinecarboxamide hydrochloride wherein the mole ratio of the indenofuran or indenothiophene compound to N-amidino-3,5-diamino-6-chloropyrazinecarboxamide hydrochloride ranges from about 50:1 to 1:1.

14. The compound of claim 4 which is racemic 4,5-dichloro-6-oxo-7-methyl-7-phenyl-1,2,7,8-tetrahydro-6H-indeno[5,4-b]furan-2-carboxylic acid.

15. A composition according to claim 11 wherein the indenofuran is 4,5-dichloro-6-oxo-7-methyl-7-phenyl-1,2,7,8-tetrahydro-6H-indeno(5,4-b) furan-2-carboxylic acid and the mole ratio of the indenofuran to N-amidino-3,5-diamino-6-chloropyrazinecarboxamide hydrochloride is in the ratio of from 10:1 to 2:1.

* * * * *